| United States Patent [19] | [11] Patent Number: 4,812,589 |
| Prater et al. | [45] Date of Patent: Mar. 14, 1989 |

[54] POLYHYDROXYL COMPOUNDS CONTAINING A SULFONIC ACID ESTER GROUP

[75] Inventors: Klaus Prater, Krefeld; Walter Uerdingen; Heinrich Heine, both of Leverkusen; Dieter Freitag, Krefeld, all of Fed. Rep. of Germany

[73] Assignee: Bayer Aktiengesellschaft, Leverkusen, Fed. Rep. of Germany

[21] Appl. No.: 908,435

[22] Filed: Sep. 17, 1986

[30] Foreign Application Priority Data

Oct. 1, 1985 [DE] Fed. Rep. of Germany ....... 3534929

[51] Int. Cl.$^4$ ............................................. C07C 143/68
[52] U.S. Cl. ......................................... 558/51; 558/46
[58] Field of Search ................................... 558/51, 46

[56] References Cited

U.S. PATENT DOCUMENTS

| 3,236,873 | 2/1966 | Brown et al. | 260/456 |
| 4,189,562 | 2/1980 | Dieterich | 558/51 X |
| 4,201,852 | 5/1980 | Dieterich | 558/51 X |
| 4,277,417 | 7/1981 | Varma | 558/51 |

OTHER PUBLICATIONS

"Organikum", 13th Edition, p. 608, Berlin, 1974.

*Primary Examiner*—Nicky Chan
*Attorney, Agent, or Firm*—Gene Harsh; Joseph C. Gil; Aron Preis

[57] ABSTRACT

The invention relates to a process for the production of sulphonic acid ester group-containing polyhydroxyl compounds having an average hydroxyl functionality of from 1.5 to 4, comprising reacting (a) paraffin sulphochlorides which are obtained by sulphochlorination of paraffins containing from 10 to 18 carbon atoms or of industrial mixtures of these paraffins, with unreacted paraffins and/or with chloroparaffins, having saponifiable chlorine content, based on the total weight of component (a), of from 5 to 15% with (b) an alcohol which is at least trihydric and which contains primary and/or secondary hydroxyl groups within the molecular weight range of from 92 to 250 or with mixtures of polyhydric alcohols having a molecular weight in the range of from 62 to 250 with an average hydroxyl functionality of from 2.5 to 5 in the presence of hydrogen chloride acceptors while maintaining an equivalent ratio of hydroxyl groups to sulphochloride groups of at least 2:1 with the optional removal of sulphochloride group-free paraffin and/or chloroparaffin and excess alcohol from the reaction mixture after the reaction.

3 Claims, No Drawings

POLYHYDROXYL COMPOUNDS CONTAINING A SULFONIC ACID ESTER GROUP

FIELD OF THE INVENTION

This invention relates to a process for the production of novel polyhydroxyl compounds which contain a sulphonic acid ester group by reacting a paraffinsulphochloride with a polyhydric alcohol, to the compounds obtained by this process and to their use as polyol components in cast resin formulations based on organic polyhydroxyl compounds and organic polyisocyanates.

BACKGROUND OF THE INVENTION

The production of cast resins, for example for the electrical industry, by reaction of organic polyisocyanates with polyhydroxyl compounds is already known (see, for example, Kunststoff-Handbuch, Vol. VII, "Polyurethane" by Becker/Braun Carl Hanser Verlag Munich, Vienna (1983) pages 410 to 425). Shaped articles of this type which are used, for example, as insulators in the electrical industry, must be substantially bubble-free and foam-free. According to the prior art, importance is placed on careful degassing and drying of the starting materials, in particular the polyhydroxyl compounds. Generally speaking, further water absorption agents such as (anhydrous) zeolites are also added to the reaction mixtures, in order to reliably prevent bubble formation caused by the reaction between isocyanate groups and water which takes place with elimination of carbon dioxide. Furthermore, the presence of water during hardening cannot be avoided in specific applications, for example in the case of cable casting compositions which have to be processed in the open air even during bad weather conditions. In this case, the conventional PUR casting compositions based on polyether polyols lead to marked foaming even if the starting materials are free from water, due to the use of water absorption agents, resulting in that the insulating effect of the cast resin is greatly impaired.

Foaming does not occur if castor oil is used instead of polyether polyols. However, this natural product is subject to great variations in quality and, furthermore, PUR molding compositions based on this polyester polyol are very susceptible to hydrolysis. A further disadvantage of the composition based on castor oil resides in the fact that they become brittle during prolonged storage at elevated temperatures (>50° C.). The poor behavior during thermal aging is due to the double bond contained in the ricinoleic acid. As a result, the cast resin compositions in the course of time, develop cracks which have a detrimental effect on the electrical insulating capacity.

As has now surprisingly been found, sulphonic acid ester group-containing polyhydroxyl compounds of the invention represent a novel type of organic polyhydroxyl compound having the above-mentioned advantages of castor oil without its disadvantages. According to the invention these polyhydroxyl compounds are obtained by a reaction of paraffin sulphochlorides with a polyhydric alcohol. When using these new polyhydroxyl compounds as the polyol component in cast resin formulations based on organic polyhydroxyl compounds and organic polyisocyanates, optionally along with conventional polyether polyols, bubble free products which also exhibit excellent stability to hydrolysis, are obtained on hardening of the cast resin composition even in the presence of water.

It is known that sulphonic acid esters can be produced by the reaction of sulphochlorides of aliphatic or aromatic sulphonic acids with aliphatic alcohols in the presence of hydrogen chloride acceptors (Organikum, 13th edition, page 608, VEB Deutscher Verlag der Wissenschaften). Sulphonic acid ester group-containing polyhyroxyl compounds based on paraffin-sulphochlorides and polyhydric alcohols have not yet been disclosed hitherto, however. Consequently, the excellent suitability of these polyhydroxyl cmpounds in cast resin formulations of the above-mentioned type was also completely unforeseeable.

SUMMARY OF THE INVENTION

The invention relates to a process for the production of sulphonic acid ester group-containing polyhydroxyl compounds having an average hydroxyl functionality of from 1.5 to 4, comprising reacting
  (a) paraffin sulphochlorides which are obtained by sulphochlorination of paraffins containing from 10 to 18 carbon atoms or of industrial mixtures of these paraffins, with unreacted paraffins and/or with chloroparaffins, having saponifiable chlorine content, based on the total weight of component (a), of from 5 to 15% with
  (b) an alcohol which is at least trihydric and which contains primary and/or secondary hydroxyl groups within the molecular weight range of from 92 to 250 or with mixtures of polyhydric alcohols having a molecular weight in the range of from 62 to 250 with an average hydroxyl functionality of from 2.5 to 5
in the presence of hydrogen chloride acceptors while maintaining an equivalent ratio of hydroxyl groups to sulphochloride groups of at least 2:1 with the optional removal of sulphochloride group-free paraffin and/or chloroparaffin and excess alcohol from the reaction mixture after the reaction.

The invention also relates to the sulphonic acid ester group-containing polyhydroxyl compounds obtained by this process.

The invention also relates to the use of the sulphonic acid ester group-containing polyhydroxyl compounds obtained by this process as the polyol component in cast resin formulations based on mixtures of organic polyhydroxyl compounds and organic polyisocyanates which react to form polyurethanes.

DETAILED DESCRIPTION OF THE INVENTION

Reactants in the process according to the invention are
  (a) paraffin sulphochlorides and
  (b) polyhydric alcohols.

Suitable starting materials (a) include the known sulphochlorination products of paraffins containing from 10 to 18 caron atoms or of industrial mixtures of these paraffins of the type which may be obtained in known manner by sulphochlorination of the paraffins, that is by treatment with sulphur dioxide and chlorine and irradiation with shortwave light. The paraffins used for this purpose may be straight-chained and/or branched. The component (a) used in the process according to the invention may comprise a mixture of paraffin sulphochlorides with unreacted paraffins and/or with chloroparaffins, the paraffin sulphochlorides may optionally contain chlorine substituents. The content of saponifiable chlorine, mainly originating from the sulphochloride groups, is essential for rendering these mixtures suitable for the process according to the invention. The saponifiable chlorine content of the mixtures is generally between 5 and 15%, preferably between 5 and 9% by weight. The non-saponifiable chlorine optionally existing in the form of aliphatic chloride substituents is not included in this calculation. The mixtures can be used as such in the process according to the invention. The separation of the unreacted paraffin and the sulphochloride-group-free chlorinated paraffin may follow the reaction according to the invention.

The alcohols (b) are polyhydric aliphatic alcohols containing primary and/or secondary hydroxyl groups. Component (b) either consists of an alcohol which is at least trihydric and has a molecular weight within the range of from 92 to 250 or of a mixture of polyhydric alcohols having molecular weights within the range of from 62 to 250 and having an average hydroxyl functionality of from 2.5 to 5. Suitable polyhydric alcohols include ethylene glycol, 1,2- or 1,3-dihydroxypropane, the various isomeric butanediols, in particular 1,4-dihydroxybutane, the various isomeric hexanediols, in particular 1,6-hexanediol, glycerine, trimethylolpropane, pentaerythritol, sorbitol or mannitol. Trimethylolpropane is used particularly preferably in the process according to the invention. It is fundamentally also possible to use low molecular weight alkoxylation products, for example ether group-containing derivatives of the above-mentioned polyhydric alcohols provided their molecular weight is within the specified ranges. The use of these ether group-containing alcohols such as diethylene glycol, triethylene alcohol, dipropylene glycol, tripropylene glycol or propoxylated trimethylolpropane is less preferred, however.

The process according to the invention is carried out in the presence of hydrogen chloride acceptors. Tertiary amines such as triethylamine, tributylamine, N,N-dimethylaniline or pyridine, in particular, are suitable for this purpose. It is particularly preferable to use triethylamine as it can easily be removed from the reaction mixture on completion of the reaction owing to its low boiling point.

When carrying out the process according to the invention, the starting materials (a) and (b) are used in quantities corresponding to an equivalent ratio of hydroxyl groups to sulphochloride groups of at least 2:1, preferably of from 2:1 to 3:1. The optionally used excess of polyhydroxyl compounds may be removed after the reaction, if desired. The sulphochloride group content of component (a) can be calculated from the content of saponifiable chlorine determined by titration. The hydrogen chloride acceptor is generally added in a quantity of from 1.02 to 1.5 equivalents, preferably from 1.1 to 1.3 equivalents based on the quantity of sulphochloride group present in component (a).

The reaction is preferably carried out in such a way that the alcohol component (b) and the hydrogen chloride acceptor are used as starting materials, the mixture is heated while stirring until there is a clear solution and component (a) is then added dropwise. Heating can then be eliminated as the reaction takes place in a weak exothermic manner. After adding component (a) the reaction mixture is allowed to continue reacting at temperatures of from 40° to 80° C., preferably from 60° to 70° C. The continued reaction time is generally from 2 to 10 hours, preferably from 3 to 7 hours.

On completion of the reaction, the hydrogen chloride acceptor (preferably tertiary amine) present in an excess is generally removed by washing with a soluble acid (for example, aqueous hydrochloric acid). Depending on the content in component (a) of sulphonic acid ester-group-free paraffins and/or chloroparaffins, two or three phases are formed, the lower aqueous phase containing the hydrochloride of amine and the optional excess alcohol and the upper organic phase(s) containing the product of the process together with unreacted paraffin and chloroparaffin. After separating the aqueous phase, the organic phase (second phase) and the combined organic phases (third phase) are dissolved in a suitable solvent (for example toluene), washed with dilute acid (for example aqueous hydrochloric acid) and subsequently washed with pure water and then dewatered by azeotropic distillation. The solvent is then removed by distillation and further volatile constituents (unreacted paraffin and/or chloroparaffin) are finally removed by vacuum distillation if desired. Substantial removal of these constituents by distillation may preferably be carried out at 13 mbar and at a sump temperature of up to 180° C., more preferably up to 150° C.

The products of the process are formed as distillation residue. These are sulphonic acid ester-group-containing polyhydroxyl compounds having an average hydroxyl functionality of from 1.5 to 4, preferably from 1.8 to 2.5. The hydroxyl functionality may be adjusted by the content of the sulfonic acid chloride groups in component (a), the functionality of the alcohol component (b) and by suitable choice of equivalent ratio of sulphonic acid chloride groups to hydroxyl groups when carrying out the process according to the invention. The new polyhydroxyl compounds generally have a hydroxyl number of from 80 to 200, preferably from 100 to 150 with an acid number of from 10 to 40, preferably from 12 to 30. They are generally substances which are liquid above about 20° C. and have a viscosity of from 400 to 3000 mPas.

The products of the process according to the invention may be used in combination with organic polyisocyanates for the production of cast resins.

Any polyisocyanates which are conventionally used in polvurethane chemistry may be used for this application according to the invention. Examples include 4,4'-diisocyanatodiphenylmethane or the industrial mixtures thereof with 2,4'- and optionally 2,2'-diisocyanatodiphenylmethane, polyisocyanate mixtures of the diphenylmethane series of the type obtained by phosgenation of aniline/formaldehyde condensates in known manner and which contain, in addition to the above-mentioned diisocyanates, varying quantities of higher homologues, 2,4-diisocyanatotoluene and the industrial mixtures thereof with up to 35% by weight, based on total mixture, of 2,6-diisocyanatotoluene, hexamethylenediisocyanate, 1-isocyanato-3,3,5-trimethyl-5-isocyanatomethylcyclohexane (isophoronediisocyanate), urethane, carbodiimide, isocyanurate, allophanate or biuret-modified polyisocyanates based on the above-mentioned unmodified polyisocyanates or any mixtures of the polyisocyanates mentioned by way of example. The corresponding polyisocyanateswwhich are liquid at room temperature are preferably used. The phosgenation products of aniline/formaldehyde condensates are particularly preferably used as organic polyisocyanates.

To produce the cast resins, the sulphonic-acid-ester-group-containing polyhydroxyl compounds according to the invention, optionally combined with up to 50 hydroxyl equivalent % of other polyhydroxyl compounds are mixed with the polyisocyanates. The equivalent ratio of isocyanate groups to hydroxyl groups is from 0.75:1 to 1.25:1, preferably from 0.9:1 to 1.1:1.

The optional polyhydroxyl compounds used in addition to the polyhydroxyl compounds according to the invention are predominantly polyether polyols having an (average) hydroxyl functionality of from 2 to 4 and (average) molecular weight which may be calculated from the hydroxyl content and the hydroxyl functionality, of from 400 to 1200. In particular, the propoxylation products of polyhydric alcohols of the type mentioned above in the description of component (b) are very suitable, but the starter molecule during the production of the polyether polyol must obviously not be identical to the alcohol (b) used in the process according to the invention. It is fundamentally also possible to use, in addition to these polyether polyols, other polyhydroxyl compounds, for example low molecular weight polyhydroxyl compounds of the type mentioned in the description of component (b) and/or castor oil during formulation of the cast resins, but this is less preferred. In any case, at least 50 hydroxyl equivalent % of the polyol component in the cast resins according to the invention comprise the sulphonic acid ester group-containing polyhydroxyl compounds according to the invention.

Conventional additives may be added to the cast resins if desired. These include, for example, (water-free) zeolite in a quantity of up to 5% by weight, based on total mixture, fillers such as ground rock, short glass fibers, polyethylene powder or other inorganic or organic fillers, pigments or accelerators known from the polyurethane chemistry.

The cast resins generally have a pot life of from 0.25 to 10 hours at room temperature and cure within a period of from 2 to 24 hours at room temperature to bubble-free plastics, the pot life and curing time being determined by the presence or absence of accelerators for the isocyanate polyaddition reaction. This period can be substantially shortened if desired by raising the temperature.

The cast resins according to the invention are particularly suitable as casting compositions in the electrical industry for the production of insulators.

The invention is further illustrated, but is not intended to be limited by the following examples in which all parts and percentages are by weight unless otherwise specified.

EXAMPLES

EXAMPLE 1

670 g of trimethylolpropane (5 mol) and 602 g of triethylamine (6 mol) were mixed in a round flask provided with stirrer, reflux condenser and thermometer, and heated to 60° C. with stirring. 2650 g of a "paraffin sulphochloride" containing 7% of saponifiable chlorine were then added dropwise within 2 hours. The "paraffin sulphochloride" used was obtained by sulphochlorination of an industrial paraffin mixture having an average chain length of 11 carbon atoms. This was a mixture containing about 50% by weight of paraffin sulphochloride, the remainder being unreacted paraffins and chloroparaffins. The equivalent ratio of hydroxyl groups to sulphochloride groups was about 3:1. A reaction temperature of from 60° to 70° C. was maintained during the dropwise addition of the "paraffin sulphochloride". After addition, the mixture was stirred for a further 4 hours at from 60° to 70° C. The reaction mixture was then washed twice with 250 ml of 10% hydrochloric acid in each case. The three phases were formed during this process of which the lower aqueous phase contained the amine hydrochloride. The middle phase contained the majority of the product of the process mixed with minor quantities of paraffins and chloroparaffins, while the upper phase was composed substantially of unreacted paraffins and chloroparaffins. The two upper phases were combined, dissolved in 500 ml of toluene and washed with 250 ml of 10% hydrochloric acid and subsequently with 250 ml of water. The toluene solution was then dewatered azeotropically and the toluene removed by distillation up to a sump temperature of 140° C. After cooling to 60° C., volatile constituents were removed by distillation under vacuum (13 mbar), the sump temperature in the final phase of distillation rose to 150° C.

2023 g of a sulphonic acid ester group-containing polyhydroxyl compound according to the invention having acid number 13, hydroxyl number 147 and a viscosity (20° C.) of 2200 mPa.s were thus formed as distillation residue.

EXAMPLE 2

100 g of the polyhydroxyl compound according to the invention from Example 1 were mixed with 10 g of zeolite paste, i.e. a mixture of 50% castor oil and 50% water-free zeolite. 37 g of a polyisocyanate mixture from the diphenylmethane series (phosgenation product of an aniline formaldehyde condensate with a NCO content of 31% and a viscosity at 23° C. of 120 mPa.s) were then stirred in. The cast resin composition thus obtained had a pot life of about 8.5 hours. The following properties were measured on a 4 mm thick plate which had been hardened for 24 hours at room temperature and 24 hours at 80° C.:
Shore A hardness: 35
Tearing strength: 0.85 N/m$^2$
Elongation: 55%
Water absorption after 24 h storage at room temperature: 40 mg.

EXAMPLE 3

80 g of the polyhydroxyl compound according to the invention from Example 1 were mixed with 20 g of a hydroxyl group-containing polyether polyol with a hydroxyl group content of 11% and a viscosity at 25° C. of 600 mPa.s (propoxylation product of trimethylolpropane) and 10 g of zeolite paste according to Example 2. This polyol component was then mixed with 44 g of the polyisocyanate according to Example 2. The resultant cast resin formulation had a pot life of 100 min at room temperature. After curing for 24 hours at room temperature and then for 24 hours at 80° C., the following values were measured on a 4 mm thick plate:
Shore A hardness: 99
Shore D hardness: 67
Tearing strength: 17.1 N/mm$^2$
Elongation: 2.5%
Notched bar toughness: 2.6 kJ/m$^2$
Water absorption: 23.9 mg

EXAMPLE 4

50 g of the polyurethane casting composition described in Example 3 were poured into a beaker glass containing 5 g of water. The cast resin composition was cured at room temperature in the presence of water.

After hardening, a compact casting exhibiting no foaming on the surface was obtained.

EXAMPLE 4a (COMPARISON EXAMPLE TO EXAMPLE 4)

Example 4 is repeated with the sole difference that the polyhydroxyl compound according to the invention according to Example 1 was replaced by an equivalent quantity of a polypropylene glycol having OH number 90 in the formulation. The reaction mixture foamed to about twice the volume during curing in the presence of water.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of a polyhydroxyl compound which contains at lest one sulphonic acid ester group, said compound being characterized in having an average hydroxyl functionality of from 1.5 to 4 comprising
    (i) reacting
        (a) at least one paraffin sulphochloride which is obtained by sulphochlorination of a paraffin containing from 10 to 18 carbon atoms and having a saponifiable chlorine content based on the total weight of component (a), of from 5 to 15% with
        (b) an alcohol which is at least trihydric and which contains primary and/or secondary hydroxyl groups having a molecular weight of from 92 to 250 or with a mixture of polyhydric alcohols having molecular weights of from 62 to 250 and an average hydroxyl functionality of from 2.5 to 5,
    in the presence of a hydrogen chloride acceptor while maintaining an equivalent ratio of hydroxyl groups to sulphochloride groups of at lest 2:1, to form an organic phase which contains said polyhydroxyl compound,
    (ii) dissolving said organic phase in a suitable solvent,
    (iii) washing said phase with dilute acid and then with water and then dewatering said phase by azeotropic distillation and
    (iv) removing said solvent by distillation.

2. The process of claim 1 wherein trimethylolpropane is used as component (b).

3. The process of claim 1 wherein said suitable solvent is toluene.

* * * * *